United States Patent [19]

Jewell, Jr. et al.

[11] Patent Number: 4,677,211
[45] Date of Patent: Jun. 30, 1987

[54] PREPARATION OF LACTONES

[75] Inventors: Charles F. Jewell, Jr., Atlanta, Ga.; James R. Wareing, Randolph, N.J.

[73] Assignee: Sandoz Pharmaceuticals Corp., E. Hanover, N.J.

[21] Appl. No.: 759,537

[22] Filed: Jul. 26, 1985

Related U.S. Application Data

[63] Continuation-in-part of Ser. No. 626,294, Jun. 29, 1984, abandoned.

[51] Int. Cl.[4] .......................... C07F 7/08; C07F 7/18; C07C 69/76
[52] U.S. Cl. .................................. 548/491; 260/408; 260/410.5; 260/410.9 R; 548/406; 549/214; 549/292; 549/407; 549/417; 549/209; 556/437; 560/56; 560/59; 560/60; 562/466
[58] Field of Search .................... 260/410.9 Q, 413 R, 260/408, 410.5; 549/292; 568/430; 560/119, 183, 56, 59, 60; 556/438, 437; 548/491

[56] References Cited

U.S. PATENT DOCUMENTS 3,637,721  1/1972  Pappas ............................... 568/430
4,420,491 12/1983  Albers-Schonberg .............. 560/119
4,450,171  5/1984  Hoffman ............................ 560/119

OTHER PUBLICATIONS

Maercker, "Organic Reactions," vol. 14, pp. 270–377, John Wiley & Sons, Inc., (1965).
Reese, "Protective Groups in Organic Chemistry," pp. 95, 103 & 104, Plenum Press, (1973).

*Primary Examiner*—Michael L. Shippen
*Attorney, Agent, or Firm*—Gerald D. Sharkin; Richard E. Vila; Frederick H. Weinfeldt

[57] ABSTRACT

7-Substituted lower alkyl hept-6-enoates and 4-hydroxytetrahydropyran-2-ones bearing 6-olefinic substituents (e.g.,) ethyl erythro-3,5-dihydroxy-7-phenyl-hept-6-enoates are prepared by a multi-step process. The process involves 3-protected-lower alkyl 3,5-dihydroxy-hept-6-enoates, which are obtained by cleaving corresponding 6α-vinyl-4β-protected hydroxy-tetrahydro 2H-pyran-2-ones. The final products are useful as anti hypercholesteremic agents.

16 Claims, No Drawings

PREPARATION OF LACTONES

This is a continuation-in-part of pending application Ser. No. 626,294 (filed June 29, 1984) now abandoned.

This invention relates to a process for preparing organic compounds, and more specifically for preparing hydroxy-tetrahydropyran-2-ones having 6-olefinic substituents and 7-substituted hept-6-enoic acid derivatives, as well as intermediates, per se in the process.

This invention provides a novel process for the preparation of trans olefins of the formula I:

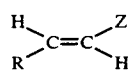

wherein R is a phenyl structure of formula A:

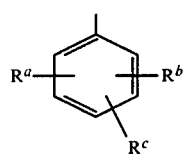

(A)

in which each of the $R^a$, $R^b$ and $R^c$ is independently hydrogen; halogen; $C_{1-4}$ alkyl; $C_{1-4}$ haloalkyl; phenyl; or phenyl substituted by halogen; $C_{1-4}$ alkoxy; $C_{2-8}$ alkanoyloxy; $C_{1-4}$ alkyl or $C_{1-4}$ haloalkyl; or $OR^d$ in which $R^d$ is any of hydrogen, $C_{2-8}$ alkanoyl, benzoyl, phenyl, halophenyl, phenyl $C_{1-3}$ alkyl, $C_{1-9}$ alkyl, cinnamyl, $C_{1-4}$ haloalkyl, allyl, cycloalkyl-$C_{1-3}$-alkyl, adamantyl-$C_{1-3}$-alkyl, or substituted phenyl-$C_{1-3}$-alkyl in each of which the substituents are selected from the group consisting of halogen, $C_{1-4}$ alkoxy, $C_{1-4}$ alkyl, or $C_{1-4}$ haloalkyl;

a naphthyl or tetrahydronaphthyl structure of the formula B:

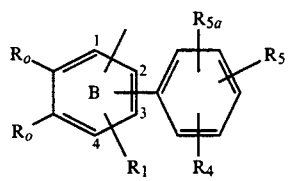

B wherein the two $R_o$ groups together form a radical of the formula

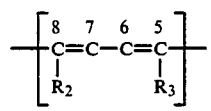

or —CH$_2$CH$_2$CH$_2$CH$_2$—, wherein $R_2$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy;

$R_3$ is hydrogen, $C_{1-3}$alkyl, $C_{1-3}$alkoxy, trifluoromethyl, fluoro, chloro, phenoxy or benzyloxy;

with the provisos that not more than one of $R_2$ and $R_3$ is trifluoromethyl, not more than one of $R_2$ and $R_3$ is phenoxy, and not more than one of $R_2$ and $R_3$ is benzyloxy;

$R_1$ is hydrogen, $C_{1-6}$alkyl not containing an asymmetric carbon atom, fluoro, chloro or benzyloxy;

$R_4$ is hydrogen, $C_{1-3}$alkyl, n-butyl, i-butyl, t-butyl, $C_{1-3}$alkoxy, n-butyoxy, i-butoxy, trifluoromethyl, fluoro, chloro, phenoxy or benzyloxy;

$R_5$ is hydrogen, $C_{1-3}$alkyl, $C_{1-3}$alkoxy, trifluoromethyl, fluoro, chloro, phenoxy or benzyloxy;

$R_{5a}$ is hydrogen, $C_{1-2}$alkyl, $C_{1-2}$alkoxy, fluoro or chloro;

with the provisos that not more than one of $R_4$ and $R_5$ is trifluoromethyl, not more than one of $R_4$ and $R_5$ is phenoxy, and not more than one of $R_4$ and $R_5$ is benzyloxy; with the proviso that on ring B the free valence and ring A are ortho- to each other; or an indol-type radical of the formula C:

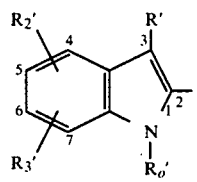

C wherein one of R′ and $R_o′$ is

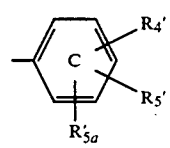

and the other is primary or secondary $C_{1-6}$alkyl not containing an asymmetric carbon atom, $C_{3-6}$cycloalkyl or phenyl(CH$_2$)$_m$—, wherein $R_4′$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy;

$R_5′$ is hydrogen, $C_{1-3}$alkyl, $C_{1-3}$alkoxy, trifluoromethyl, fluoro, chloro, phenoxy or benzyloxy;

$R_{5a}′$ is hydrogen, $C_{1-2}$alkyl, $C_{1-2}$alkoxy, fluoro or chloro; and m is 1, 2 or 3;

with the provisos that both $R_5′$ and $R_{5a}′$ must be hydrogen when $R_4′$ is hydrogen; $R_{5a}′$ must be hydrogen when $R_5′$ is hydrogen; not more than one of $R_4′$ and $R_5′$ is trifluoromethyl; not more than one of $R_4′$ and $R_5′$ is phenoxy and not more than one of $R_4′$ and $R_5′$ is benzyloxy;

$R_2′$ is hydrogen, $C_{1-3}$alkyl, n-butyl, i-butyl, t-butyl, $C_{3-6}$cycloalkyl, $C_{1-3}$alkoxy, n-butoxy, i-butoxy, trifluoromethyl, fluoro, chloro, phenoxy or benzyloxy;

$R_3′$ is hydrogen, $C_{1-3}$alkyl, $C_{1-3}$alkoxy, trifluoromethyl, fluoro, chloro, phenoxy or benzyloxy;

with the provisos that $R_3′$ must be hydrogen when $R_2′$ is hydrogen; not more than one of $R_2′$ and $R_3′$ is trifluoromethyl; not more than one of $R_2′$ and $R_3′$ is phenoxy; and not more than one of $R_2$ and $R_3$ is benzyloxy; and Z is

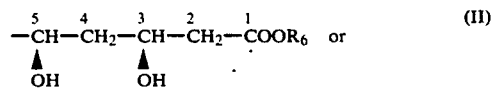

(II)

-continued $$\text{(III)} \quad \underset{\underset{O}{\overset{6}{\|}}{\overset{\|}{C}}}{\overset{5}{\underset{O}{\overset{CH_2}{\diagdown}}}} \overset{4}{\underset{CH_2}{\overset{OH}{\diagup}}} C^{\text{IIIIH}}_3,$$

wherein $R_6$ is hydrogen, $C_{1-3}$alkyl, n-butyl, i-butyl, t-butyl, benzyl; or M;

wherein M is a pharmaceutically acceptable cation.

The compounds of formula I constitute 3 classes of compounds depending on the nature of R, namely (1) compounds IA, where R is of formula A, IB where R is of formula B, and of IC when R is of formula C. Within the main classes, subclass can be seen, such as type IB-1 where $R_o+R_o$ is an alkadienyl chain and type IB-2 where $R_o+R_o$ is a alkylene chain; types IC-1 and IC-2 depending upon whether Ring C is at position-1 or -3.

Compounds I are those in which (1) when Z is of type II the alcohol oxygens have the erythro relationship and (2) when Z is of type III the alcohol oxygen at the carbon-3 and the substituent at carbon-6 are trans to each other.

Compounds IA are known and described in U.S. Pat. No. 4,308,378 (issued Dec. 29, 1981) and European Pat. No. 11,928 (published June 11, 1980) wherein the compounds are disclosed to be useful as anti-hyper-cholesteremic agents. Compounds IB are disclosed in PCT Application WO 84/02903 (published Aug. 2, 1984) and pending application Ser. No. 570,584 filed on Jan. 13, 1984, now abandoned. Compounds IC are disclosed in PCT Application WO 84/02131 (published June 7, 1984) and pending application Ser. No. 722,288 filed Nov. 11, 1984. Compounds IB and IC are also useful as anti-hyperchlolesteremic agents as they are inhibitors of cholesterol biosynthesis in the manner of the known products compactin and mevinolin and are therefore useful in the treatment of atherosclerosis, as described in said applications.

The terms "halogen" and "halo" as used in the definition of compounds IA is intended to include fluoro and chloro.

An embodiment of this invention is a multi-step process for the preparation of compounds I, which process may conveniently be represented by Reaction Scheme A, below, wherein R is as defined above. $R_6'$ is the same as $R_6$ when it is not hydrogen or M, and $P^1$ is a protecting (or masking) group for a hydroxy function; and $R_7$ and $R_8$ are, independently, hydrogen or alkyl, e.g. having from 1 to 6 carbon atoms, such as methyl. Preferably, at least one of $R_7$ and $R_8$ is hydrogen, and more preferably both $R_7$ and $R_8$ are hydrogen. The final products I are shown as compounds I' where Z is of type II and $R_6$ is $R_6'$; I'' where $R_6=$H or M, and I''' where Z is of type III.

REACTION SCHEME A

[Structure A: $H-\underset{\underset{R_7}{\overset{\|}{C}}}{\overset{OH}{C}}\underset{R_8}{\diagdown}\underset{\diagup}{\overset{OP^1}{C}}\underset{\diagdown}{\overset{O}{\|}}{C}-OR_6'$]

↓ protection process (a)

[Structure C: $H-\underset{\underset{R_7}{\overset{\|}{C}}}{\overset{OP^1}{C}}\underset{R_8}{\diagdown}\underset{\diagup}{\overset{OP^1}{C}}\underset{\diagdown}{\overset{O}{\|}}{C}\,OR_6'$]

↓ $O_3$ oxidation process (b)

[Structure D: $O=\underset{H}{\overset{OP^1}{C}}\underset{\diagdown}{\overset{OP^1}{\diagup}}\underset{\diagup}{\overset{O}{\|}}{C}\,OR_6'$]

↓ Wittig Reax. process (c)

[Structure E: $H-\underset{\underset{R}{\overset{\|}{C}}-H}{\overset{OP^1}{C}}\underset{\diagdown}{\overset{OP^1}{\diagup}}\underset{\diagup}{\overset{O}{\|}}{C}\,OR_6'$]

↓ deprotection process (d)

[Structure I': $H-\underset{\underset{R}{\overset{\|}{C}}-H}{\overset{OH}{C}}\underset{\diagdown}{\overset{OH}{\diagup}}\underset{\diagup}{\overset{O}{\|}}{C}\,OR_6'$]

process (e) ↙      ↘ process (g)

I'' $\xrightarrow{\text{process (f)}}$ I'''

The process steps of Reaction Scheme A are discussed individually below.

In process (a), a compound A is converted to a corresponding compound C by conversion of the hydroxy function to its protected form. Process (a) may be accomplished by reacting a compound A with a protecting group-bearing reagent of the formula B:

$$P^1-L \qquad\qquad B$$

in which $P^1$ is as defined above and L is a leaving group, in the presence of an acid acceptor, e.g., imidazol, in an inert medium, e.g., a liquid amide, such as dimethyl formamide (DMF) at moderate temperatures, e.g., from about 5° to 40°, under essentially anhydrous conditions. Leaving groups are well known in the art, and include higher halo, i.e., chloro, bromo, or iodo, preferably chloro, and alkyl and aryl sulfonyl, radicals, e.g., $C_1-C_6$ alkyl or phenyl which may be unsubstituted or monosubstituted by a $C_1-C_4$ alkyl, such as p-toluene sulphonyl.

Suitable protective groups $P^1$, include tri-substituted silyl radicals having at least 2, and preferably 3 bulky radicals, i.e. radicals selected from the group consisting of (a) tertiary alkyl (C₄ to C₈) groups especially t-butyl, and (b) aryl, preferably phenyl which may be unsubstituted or substituted by up to 2 (preferably 0 or 1) of any of lower alkyl (C₁–C₄), chloro, nitro, trifluoromethyl, or mono-substituted in the para-position by phenyl or benzyl (which may be unsubstituted or in turn substituted by one or two of such groups as mentioned above, especially at the para-position) and the remaining substituent, where present, is a non-bulky radical, eg. unbranched alkyl having from 1 to 4 carbon atoms, eg. methyl.

A preferred P¹ is the diphenyl tertiary-butylsilyl radical and a preferred reagent of formula B is chlorodiphenyl t-butylsilane. Alternatively, P¹ may be lower alkyl, e.g. having from 1 to 4 carbon atoms, such as methyl.

In process (b) compounds C are converted to corresponding compounds D by oxidation of the vinyl group to an aldehedic function. The oxidation may be obtained by conventional means for oxidizing an olefinic position to a carbonyl function. A particularly convenient method of carrying out process (d) is by treating a compound C in an inert medium e.g. a chlorinated hydrocarbon, such as methylene chloride, methanol or ethyl acetate, with ozone at reduced temperatures, e.g. at from about −50° to −80° C. e.g. about −78° C. When the required amount of ozone has been reacted, the intermediate ozonide is decomposed by the addition of a mild reducing agent, such as dimethyl sulfide or triphenylphosphine to the reaction mixture to yield the desired aldehyde; a preferred method being use of ethyl acetate and triphenylphosphine.

Final steps in the process are the reaction (process c) of the protected di-hydroxy aldehyde (D) with a Wittig reagent bearing the desired R-moiety (a compound $X^o$) to give a protected di-hydroxy form of a final product (E), which is then deprotected (process d) to yield a desired final product I' which may then be converted to final compounds I'' or I''' as desired.

In process (c) Wittig reagents have the formula $X^o$:

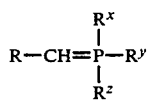   $X^o$ wherein R is as defined above and each of $R^x$, $R^y$ and $R^z$ is, independently, an aryl radical. Process (c) is conveniently carried out in an inert medium, e.g., a cyclic ether such as tetrahydrofuran at reduced temperatures, e.g. −15° to +5° C., such as −10° to 0° C. under essentially anhydrous conditions.

The Wittig reagents $X^o$ are prepared by treating a compound of formula X:

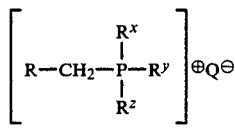   X in which R, $R^x$, $R^y$, $R^z$ are as defined above, and Q is a higher halo (having an atomic weight of from about 34 to 120), e.g., chloro, bromo or iodo, with a strong base, such as an alkali metal salt of a hydrocarbon, e.g., n-butyl lithium, in an inert medium, such as a cyclic ether, at reduced temperatures, e.g., from about −15° to 0° C., e.g., about −10° C. Conveniently the Wittig reagent is used in situ, so that the conditions and medium employed in its preparation are also utilized in its reaction with a compound E, i.e. in process (e).

In the Wittig reagents, any of $R^z$, $R^x$ or $R^y$ is preferably phenyl which is unsubstituted or substituted by one or two lower alkyl (C₁–C₄) or chloro substituents. Preferably $R^x$, $R^y$ and $R^z$ are the same.

The above-mentioned compounds of formula X are obtainable in the conventional method for preparing such reagents; a convenient method is by reacting a compound of the formula X':

   X' in which R and Q are as defined above, with a phosphine of the formula X'':

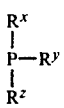   X'' in which $R^x$, $R^y$ and $R^z$ are as defined above, e.g. triphenyl phosphine, in an inert anhydrous organic solvent, for example a hydrocarbon such as benzene, toluene or xylene, or a mixture thereof, at a ratio of about 1–1.1 moles of phosphine (X'') per mole of halide (X'). The reaction temperature is conveniently 60° C. to reflux, preferably not in excess of 150° C., and, while the reaction time is inversely related to the reaction temperature, it is conveniently 2–8 hours. The reaction is run under essentially anhydrous conditions, e.g. in an inert atmosphere.

Compounds X' are obtainable by halogenating a corresponding alcohol of the formula X''':

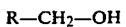   X''' in which R is as defined. The halogenation may be carried out in the conventional manner. Compounds X''', in turn are obtainable by reducing esters of formula $X^{IV}$:

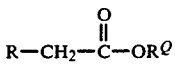   $X^{IV}$ in which R is as defined above and $R^Q$ is methyl or ethyl preferably methyl. Compounds $X^o$ are conveniently prepared by the method disclosed in application Ser. Nos. 722,288 (filed Nov. 11, 1984 and 570,584 (filed Jan. 13, 1984), now abandoned, noted above; said applications being incorporated by reference herein.

In process (d) the deprotection of a compound E to its corresponding compound I', may be accomplished in the conventional manner. Where the protecting group is a silyl-type, then fluoride or acid treatment is employed, e.g., using a mixture of at least equal (e.g. 2 times) molar portions of acetic acid and tetrabutylammonium fluoride (TBAF) in THF, methanolic HCl, or fluoride anion reagents. Moderate temperatures may be employed, e.g., from about 20° to 60°, e.g., 20° to 30° C. When P¹ is alkyl, then deprotection may be accomplished by treatment with BBr₃ in methylene chloride at about −23° C.

In process (e) a compound I', i.e. the deprotected form of a compound E, is saponified. This is achieved by treatment with aqueous alkali metal base, e.g., sodium hydroxide, preferably in a water-miscible co-solvent, e.g. dioxane, at reduced temperatures, e.g. from about −5° to +10° C., such as in an ice bath. Where a product is desired in which $R_6$ is hydrogen, i.e., the free acid form, such is obtained by acidifying the salt form (where $R_6$=M) by conventional means, e.g., by addition of dilute hydrochloric acid.

Process (f) is accomplished by heating a compound I'' in which $R_6$=H, in an inert medium, e.g. an aromatic hydrocarbon such as toluene at from about 80° to 140° C., for example at the reflux temperature of the reaction medium.

Alternatively, a compound I' may be directly converted to its corresponding compound I''' by carrying out the procedure of process (d) and heating, e.g. at about 80° to 140°, e.g. at the refluxing temperature of the reaction medium i.e. process (g).

Compounds A employed in Reaction Scheme A, above, are conveniently attainable by a series of steps as set forth in Reaction Scheme B below, wherein $P^1$, $R^7$ and $R^8$ are as defined above, and $P^2$ is a protective group.

REACTION SCHEME B

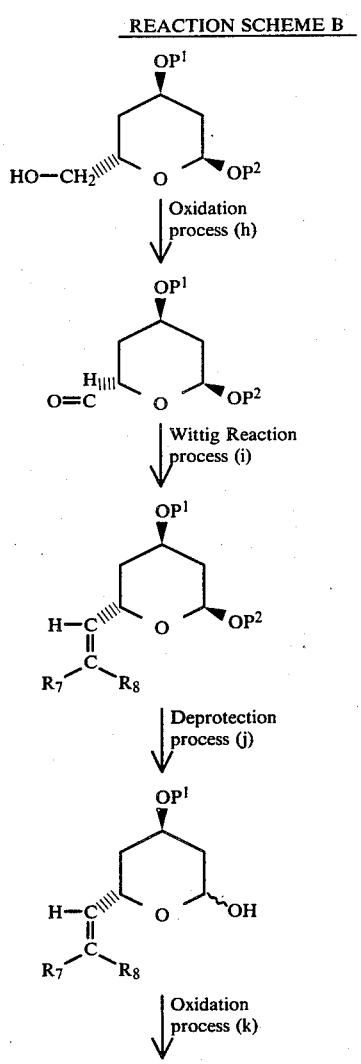

-continued
REACTION SCHEME B

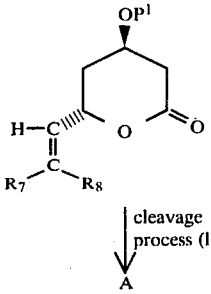

The series of process steps (h) to (k) depicted in Reaction Scheme B, above, is disclosed in U.S. Pat. No. 4,625,039 (issued Nov. 25, 1986). The preparations of alternate starting materials F and II of Reaction Scheme B, above, are disclosed in U.S. Pat. No. 4,474,971 (issued Oct. 2, 1984) (wherein they are designated as compound D and V, respectively). All of the above-mentioned patents are incorporated herein by reference.

Compounds V may be converted to corresponding compounds A (process 1) in a conventional manner for converting a delta-lactone to a delta-hydroxy ester. A convenient method of carrying out process (1) is to treat a compound V under anhydrous conditions at reduced temperature, e.g. at about −10° to +10° C., especially at about 0° C., with a alkali metal —$OR_6'$ in an alcohol corresponding to the $R_6'$ moiety, as reaction medium, e.g. using methanol/sodium methoxide, preferably in excess, e.g. 4 to 12 fold equivalents. It is convenient to quench the reaction by addition, to the reaction mixture, of aqueous solution, e.g. saturated aqueous ammonium chloride.

An advantage of this invention is that compounds I''' in the 4R,6S, enantiomer form may be prepared where starting materials have such form, e.g. compounds F; thus avoiding the difficulty of separating isomeric forms where such a form is desired.

Reagents and starting materials described herein, e.g. compounds X'' and $X^{IV}$ are known and obtainable by known means, or where not known, may be obtained by adaptation of methods reported in the literature for the preparation of known analogs; some compounds being commercially available.

The final products and intermediate compounds described herein may be recovered and refined, where such is desired, by conventional means, such as by crystallization, distillation or chromotographic techniques such as column or thin layer chromatography, e.g., silica gel column chromatography.

Evaporations are done under vacuum employing minimal heating. Drying of organic phases is done over anhydrous sodium sulfate, unless indicated otherwise.

The following examples are illustrative of the invention. All temperatures are centigrade and room temperature is 20° to 30° C., unless indicated otherwise.

When NMR characterization data is presented, the analysis is run in $CDCl_3$ and values given in ppm; digits in parenthesis are number of protons; and t=triplet, d=doublet, s=singlet, m=multiple and b is broad, and J is coupling factor, unless indicated otherwise.

EXAMPLE 1

(E), -methyl erythro-(3R,5S)-3,5-dihydroxy-7-phenylhept-6-enoate (a compound I')

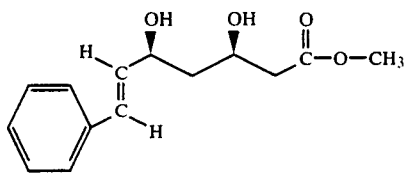

Step A, preparation of (acetato-o) (tetrahydro-4,5-dihydroxy-6-hydroxymethyl-2-methoxy-2H-pyran-3-yl)-mercury*

*may also be called (4α,5β-dihydroxy 6α-hydroxymethyl-2β-methoxy-tetrahydro-2H-pyran-3-yl) mercuric acetate

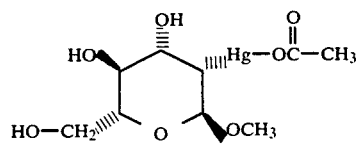

Under a nitrogen atmosphere, 300 mg of metallic sodium is dissolved in one liter of methanol (freshly distilled from magnesium) over about 10 minutes, with stirring. 136.1 g of tri-O-acetyl-D-glucal** is added (as a solid), which dissolves, and the mixture is cooled and stirred at room temperature, for one hour at which time TLC indicates methanolysis is complete. 159.35 g of mercuric acetate is slurried in one liter of freshly distilled methanol. The slurry is added to the reaction mixture through an addition funnel having a widebore stopcock, portionwise, over a period of one hour. As each portion is added, it dissolves in a short time. After the addition is completed stirring is continued (at room temperature and under nitrogen gas) for an additional four hours, at which time the reaction mixture is homogeneous and colorless. Heat is gently applied by a bath (not over 40°) to remove (under vacuum) 1,200 ml of solvent. The residue begins to solidify as it cools; and scratching the inside of the vessel over a period of about 30 minutes results in a granular solid product. The solids are collected on a sintered-glass filter, and the vessel rinsed with 50 ml. of ice-cold dry methanol, which is used to wash the filtered solids. The solids are washed with 300 ml of dry diethyl ether, and then dried (under vacuum) to obtain the title product of this step as a fine white powder. If desired, a second crop may be obtained by adding enough methanol to the mother liquor to make it homogeneous, and then concentrating to a thick oil, which solidifies on standing, and on treatment as above, yields additional product as a white solid. The product of this step, is either used promptly for the next step, or held under nitrogen if not used promptly.

**may also be called 3β,4α-dihydroxy-2α-hydroxymethyl-2,3-dihydro-2H-pyranyl triacetate.

Step B, preparation of 4α,5β-dihydroxy-6α-hydroxymethyl-2β-methoxy-tetrahydro-2H-pyran

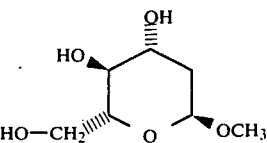

A slurry of 159.0 g of the product of step A above and one liter of methanol (freshly distilled from magnesium) is prepared. To the slurry is added 33.5 g of finely powdered solid sodium chloride. The mixture is stirred for about 5 minutes at room temperature resulting in a homogeneous solution, except for excess sodium chloride. The mixture is then cooled to 0° C. (with an external ice bath) and 10.7 g of sodium borohydride which had been finely powdered, slurried in one liter of dry isopropanol freshly distilled from BaO) is placed in an addition funnel having a wide-bore stopcock (Agitation is necessary to maintain the mixture in suspension). The slurry is added to small portions over 1.5 hrs. with ice-bath cooling in order to maintain internal temperature below 25°, as the reaction is exothermic and produces a gas and metallic mercury). When the addition is completed, the ice-bath is removed, and the suspension (gray) is allowed to stir for two hours. Solvent is vacuum distilled off (at below 40°) until the residue is almost dry, and one liter of ethyl acetate (freshly distilled from P₂O₅) is added. The slurry is cooled to about 0° and concentrated hydrochloric acid then added dropwise, with vigorous stirring. (The pH is checked after each 5 drops of the acid addition) until slightly acid. 50 g of solid sodium bicarbonate is immediately added; the entire acidification should be completed in less than 5 minutes. After stirring for about 5 minutes, 50 g of 4 Å molecular sieve is added, and the reaction mixture filtered through a pad of celite supported on glass-wool in a sintered glass funnel, pre-wetted with dry ethyl acetate. The gray sludge in the funnel is washed 3 times with 100 ml portions of dry ethyl acetate and the combined ethyl acetate extracts evaporated to a thick colorless gum. The gum is dried under high vacuum for 1 hr. then held for about 18 hrs. in a vacuum oven in the presence of P₂O₅, and then placed under high vacuum for one hour which results in a waxy solid which upon standing (5 hours) becomes less waxy. The solids are triturated with dry diethyl ether to give solid title product of this step, m.p. 64°-66° (softening at 63°).

Step C, preparation of 4α,5β-dihydroxy-2β-methoxy-6α-triphenylmethoxymethyl-tetrahydro-2H-pyran

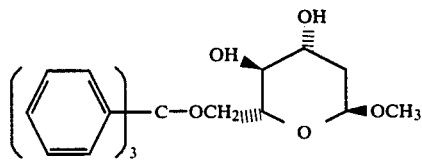

Under a nitrogen atmosphere 41.5 g of the triol product of Step B is mixed with one liter of pyridine (freshly distilled from potassium hydroxide) resulting in almost complete solution (as some solid remains in suspension, after ½ hr. stirring). 300 ml of dry dichloromethane is added with stirring, resulting in almost complete solution. 69.695 g of trityl chloride (solid) is added resulting in the solution turning slightly tan (without noticeable exotherm) and the mixture is stirred for about 18 hrs. under nitrogen during which a precipitate forms. The mixture is poured into 1.5 liters of ice-cold dilute hydrochloric acid (10%) and extracted 3 times with 200 ml portions of dichloromethane. The combined dichloromethane extracts are washed 6 times with 200 ml portions of ice-cold 10% hydrochloric acid, 2 times with 200 ml portions of saturated aqueous sodium bicarbonate, once with 200 ml of brine and then dried over anh. magnesium sulfate. The dried extracts are recovered by filtration and solvent removed under vacuum, to obtain a residue, which is a thick oil (partly solid, which smells of pyridine). The residue is redissolved in 500 ml of ethyl ether and 200 ml of dichloromethane, and the solution washed 5 times with 200 ml portions of ice-cold hydrochloric acid, twice with 200 ml portions of sat. aqueous sodium bicarbonate, once with brine, and dried over anhydrous magnesium sulfate. The dried solution (light yellow) is then evaporated under vacuum to obtain a tan foam, which is then dissolved in 200 ml of hot ethyl ether plus enough dichloromethane to make the mixture homogeneous. To the resulting solution is added pentane until cloudy, then allowed to stand at room temperature for about 48 hours, during which a precipitate forms. The solids are collected on a filter and washed with pentane to obtain the title product of this step, m.p. 140°–142°.

Step D, Preparation of 4β,5β-epoxy-2β-methoxy-6α-triphenylmethoxymethyl-tetrahydro-2H-pyran

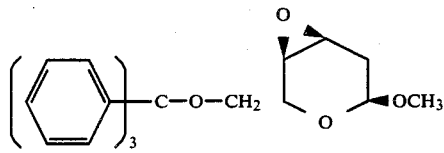

Under nitrogen, 9.6 g of sodium hydride (as a 50% dispersion in paraffin oil) is washed 3 times with 10 ml portions of pentane, 80 ml of hexamethylphosphoramide (HMPT) is added to the washed sodium hydride. 20.025 g of the diol product of Step C is dissolved in 100 ml of HMPT, the solution placed in an addition funnel and cautiously added therefrom to the mixture at room temperature over a period of about 15 minutes (gas evolves). The addition funnel is rinsed with 20 ml of HMPT and the rinse added to the mixture, which is then stirred for 1.5 hrs. at room temperature, (bubbling stops and the reaction mixture is a light tan color). The reaction mixture is diluted with 100 ml of dry THF (freshly distilled) and the mixture cooled to −30° under N₂. 16.72 g of 2,4,6-triisopropylbenzenesulfonyl imidazol in 100 ml of dry THF is added drop-wise to the mixture over a period of about 1 hr. (−30° temperature being maintained). After addition stirring is continued for 3 hrs. at −30°. The reaction mixture is filtered (through filter paper containing celite, pre-wetted with THF), and the solids washed on the filter with 100 ml of THF. The filtrate is concentrated by vacuum-evaporation to obtain a viscous oil, which is poured into 2.5 liters of brine and extracted 5 times with 150 ml portions of diethyl ether. The combined ether extracts are washed twice with 50 ml of brine, dried over anh. magnesium sulfate and evaporated to a residue (thick oil). 10 to 15 ml of dichloromethane is added to the residue which is then warmed, and pentane added to give a volume of about 300 ml. Upon standing for about 18 hours a precipitate forms which is washed with pentane and recovered as a white solid. The solid is recrystalized from pentane-diethylether to yield the title product of this step m.p. 100°–102°. Additional product can be recovered from the mother liquor, if desired. The product of this step is also known as 3,7-dioxabicyclo-[4.1.0]heptane, 2-methoxy-4-triphenylmethoxy-2β,4α,6β,7β.

Step E, Preparation of 2β-methoxy-6α-triphenylmethoxymethyl-tetrahydro-2H-pyran-4β-ol

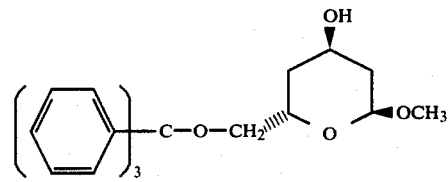

8.04 g. (20 mmole) of 4β,5β-epoxy 2β-methoxy-6α-triphenylmethoxymethyl-tetrahydro-2H-pyran is dissolved in 200 ml diethyl ether which is then cooled to 1° C. and 20 ml (20 mmole) of a 1 molar solution of lithium aluminum hydride in ether is added dropwise over five minutes maintaining the temperature at 1° C. After one hour at 1° C. and three hours at room temperature 20 ml of ethyl acetate is added slowly followed by 20 drops of H₂O. The reaction mixture is filtered through celite and the solvent removed in vacuo to give 7.51 g. crude oil which crystallizes from ether-pentane to give 5.82 g. wt. solid product. The solid is "flash chromatographed" on silica gel with 3% acetone in methylene chloride to give the title product of this step, with no trace of isomeric materials by TLC, in this fraction* GC or C¹³ NMR. m.p. 101.5–103.5

*A small amount of the isomeric 2β-6α-triphenylmethoxymethyl-tetrahydro-2-H-pyranol-5β-ol can then be recovered from the column.

[a]$_D^{25}$ +47.14 (CHCl₃) [c=2.07]

Step F, Preparation of 2β-methoxy-4β-(diphenyl t-butylsiloxy)6α-triphenylmethoxy-methyl-tetrahydro-2H-pyran;

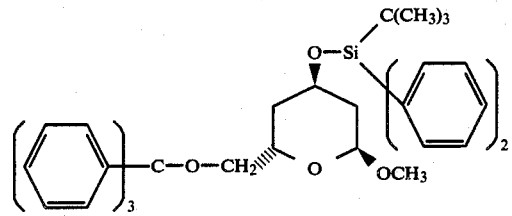

23.25 g (0.05 m) of the alcohol of Step E is dissolved in 207 ml of DMF*, 8.3 g of imidazole is added followed by 16.74 g of t-butyl diphenyl silyl chloride. When the reaction is complete, it is poured into 1 liter of brine and extracted 4 times with 200 ml portions ether. The ether phase is washed three times with 200 ml portions of cold 5% hydrochloric acid, 3 times with 200 ml portions of aqueous sat. sodium bicarbonate, dried over anh. sodium sulfate and evaporated in vacuo to a solid which is recrystallized from ether-hexane to obtain the product of this step as a white cryst. solid m.p. 151°-152° C.

*dimethylformamide

Step G, Preparation of 2β-methoxy-4β-(diphenyl t-butylsiloxy)-6α-hydroxymethyl-tetrahydro-2H-pyran; a compound F

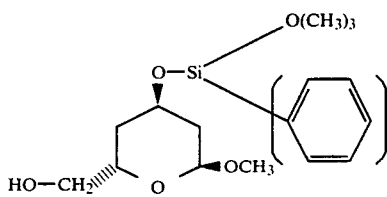

10 g (0.0156 moles) of trityl ether of Step F is dissolved in 300 ml of THF plus 30 ml of t-butyl alcohol. The solution is cooled to −40° C. and 300 ml of ammonia is condensed into the flask. Some cloudiness develops so an additional 170 ml of THF is added. The reaction is maintained at −40° C. while 2.3 g of sodium metal is added over 2 hours. When all the sodium has dissolved, a few chips of ice are added and the dark blue solution becomes colorless. The ammonia is allowed to boil off, the THF phase is filtered and then evaporated to a residue. The residue is taken up in ether, dried over anh. sodium sulfate and evaporated to obtain a residue. The residue is place on a short column of alumina (Activity III) which is eluted first with toluene to recover the by-product triphenylmethane and then with ethyl acetate to obtain the desired product of this step $[\alpha]_D^{25} = +63.56$ (CHCl$_3$, c=1.09)

Step H Preparation of [4β-(diphenyl t-butylsiloxy)-6β-methoxy-tetrahydro-2H-pyran-2-yl]-aldehyde; a compound II.

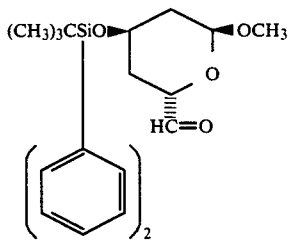

9.596 ml of oxalyl chloride dissolved in methylene chloride is cooled to −50° C. and a solution of 15.61 ml dimethyl sulfoxide (DMSO) dissolved in 50 ml methylene chloride is added at such a rate as to maintain −50° C. The mixture is stirred 2 minutes after addition is complete, followed by the addition of 4.006 g (0.01 moles) of the alcohol of Step F, dissolved in 10 ml methylene chloride over 5 minutes, maintained at −50° C. After 15 min. at −50° the mixture is treated with 69.69 ml of triethylamine in 50 ml methylene chloride and then stirred at −50° C. for 2 hours. Ten mls of brine is added and the cold reaction mixture is poured into 300 ml saturated aqueous sodium bicarbonate. The methylene chloride layer is separated, washed 3 times with aqueous sodium bicarbonate, 2 times with brine, dried over anhydrous sodium sulfate and concentrated to an oil which is chromatographed on silica gel with ether-hexane (1 to 9) to give a yellow oil, which shows carbonyl absorption at 1739 cm−1 (IR); $[\alpha]_D^{25} + 51.66$ (CHCl$_3$, c=2.07).

Step I, 6α-vinyl-4β-(diphenyl t-butylsiloxy)-2β-methoxy-tetrahydro-2H-pyran (A compound III)

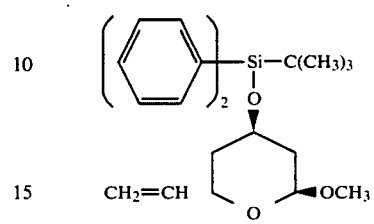

8.43 g (0.02 moles) of methyl triphenylphosphonium iodide is slurried in 150 ml of dry tetrahydrofuran under a nitrogen atmosphere and 12.9 ml of a 1.55 molar (0.02 moles) solution of butyl lithium in hexane is added dropwise over 10 minutes. The solution becomes homogeneous with a light yellow color. After cooling to 0° C., 5.52 g (0.014 moles) of the aldehyde product of Step H (II), above, dissolved in 20 ml tetrahydrofuran is added over one half hour. The reaction mixture is allowed to come to room temperature and stirred for 18 hrs. Thin layer chromatography (silica gel-methylene chloride) indicates starting material is consumed. The reaction is poured into 200 ml brine and the tetrahydrofuran is removed in vacuo, the residue is extracted four times with 200 ml portions of diethyl ether, dried over anhydrous magnesium sulfate, filtered and concentrated to a brown syrup which is "flash chromatographed" on silica gel with 9:1 methylene chloride-hexane to 3.20 g of a light yellow syrup $[\alpha_D] = +49.5$ (c=2.95, CHCl$_3$) 200 MHz NMR (CDCl$_3$) 7.65-7.75 (m, 4H), 7.3-7.45 (m, 6H), 5.7-5.9 (m, 1H), 5.03-5.3 (m, 2H), 4.7-4.8 (m, 1H), 4.7 (t(J=3 Hz),1H), 4.12 (m, 1H), 3.4 (S, 3H), 1.5-1.8 (m, 4H), 1.09 (S, 9H).

Step J, 6α-vinyl-4β-(diphenyl t-butylsiloxy)-2α+2β-hydroxy-tetrahydro 2H-pyran (a compound IV)

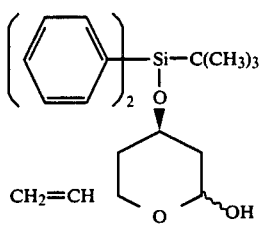

2.57 g (6.5 mmoles) of the olefinic product of step I, above, (III) is added to a mixture of 27.8 ml of glacial acetic acid, 18.5 ml of tetrahydrofuran and 18.5 ml of water and the solution heated to 70° C. When thin layer chromatography indicates starting material is gone (silica gel, 1:1 ether-hexane), i.e., about 2 hours, the solution is allowed to cool to room temperature, transferred to a one liter flask and brought to pH 7 by the addition of saturated sodium bicarbonate solution (gas evolutioon occurs). The neutral solution is concentrated in vacuo to remove tetrahydrofuran and the aqueous residue extracted twice with 200 ml portions of diethyl ether which are combined and then dried over anhyd.

magnesium sulfate, filtered, and concentrated to 2.53 g of an oil which is a mixture of lactols (title products of this step) and is used as is for the following step (K).

Step K—6α-vinyl-4β-(diphenyl t-butylsilyloxy)-3,4,5,6-tetrahydro-2H-pyran-2-one (a compound V: 4R,6S form)

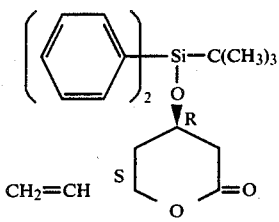

To 2.53 g (6.6 mmole) of the lactol product of step J, above, dissolved in 132 ml of methylene chloride at room temperature is added 4.26 g (20 mmoles) pyridinium chlorochromate as a solid. The reaction turns orange and then brown. After stirring for 18 hours, 350 ml of diethyl ether is added and the resulting precipitate removed via filtration through 50 g silica gel which is washed with 350 ml of diethyl ether. Concentration gives 2.41 g of a yellow oil which can be crystallized from cold hexane to give refined lactone product of this step as a white solid, m.p. 61°-62° C. IR (CH$_2$Cl$_2$) 1739 cm$^{-1}$ C=O) [α]$_D^{25}$= +6.5 (CH$_2$Cl$_2$, c=0.99)

200 MHz NMR (CDCl$_3$) 7.6–7.7 (m, 4H), 7.35–7.5 (m, 6H), 5.7–5.9 (m, 1H), 5.15–5.35 (m, 3H), 4.28 (m, 1H), 2.4–2.7, (m, 2H), 1.8–2.0 (m, 1H), 1.55–1.7 (m, 1H), 1.09 (S, 9H).

Step L—Methyl (-3R,5S)3-(diphenyl t-butylsilyloxy)-5-hydroxyhept-6-enonate (a compound A)

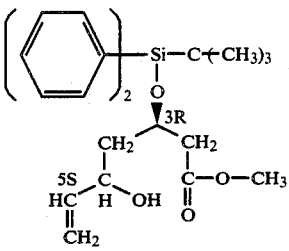

100 mg (0.26 mmole) of the lactone product of Step K, above, is dissolved in 26.3 ml dry methanol and cooled to 0° C. Solid sodium methoxide (113.6 mg., 2.11 mmole, 8 equivalents) is added thereto and the mixture stirred for one hour, quenched with 1 ml of saturated aq. ammonium chloride, diluted with 50 ml diethyl ether and washed with brine, dried, filtered and concentrated to a yellow syrup which is refined by thick layer chromatography on silica gel with methylene chloride, to obtain the title product of this step as 92.5 mg of a light yellow syrup: [α]$_D^{25}$= -7.06° (CHCl$_3$,c=1.09)

IR(thin film)3460(—OH), 1726(C=C)cm$^{-1}$, 200 MHz NMR (CDCl$_3$) 7.3–7.9(m, 10H), 5.6–5.8(m, 1H), 4.95–5.15(m, 2H), 4.38(m, 1H), 4.25(M, 1H), 3.55(S, 3H), 2.55[d(J=6 Hz), 2H], 2.1(m, 1H), 1.6–1.8(m, 2H), 1.06(S, 9H).

Step M—Methyl (-3R,5S-) 3,5-di(diphenyl t-butylsilyloxy)-hept-6-enoate (a compound C)

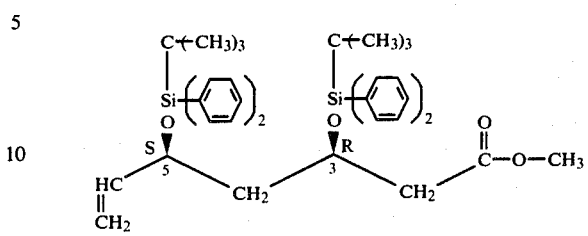

To 23.6 mg (0.057 mmole) of the heptenoate product of Step L, above, in 1 ml of dry dimethylformamide, is added 15.6 mg (0.687 mmole, 12 equivalents) of imidazole and then 89.6 μl (0.342 mmole) of neat tert-butyl diphenylsilyl chloride and 5 mg of p-dimethylaminopyridine. The solution is stirred at room temperature for 48 hours. The reaction product is recovered by pouring the reaction mixture into 75 ml brine, extracting twice with 50 ml portions of diethylether and the combined extracts dried, filtered and concentrated to yield the crude title product of this step as an oil which can be refined by thick layer chromatography on a silica gel plate, eluting with 1:3 diethyl ether:hexane. The refined product (R$_f$=0.77), 30 mg, is recovered as a colorless oil; IR (thin film) 1727 (C=O) cm−1; 200 MHz NMR (CDCl$_3$) 7.2–7.6(m, 20H), 5.43(m, 1H), 4.7(m, 2H), 4.2(m, 2H), 3.5(S, 3H), 2.47[dd(J$_1$=15 Hz,J$_2$=5 Hz)1H]; 2.3[dd(J$_1$=15 Hz,J$_2$=7 Hz),1H], 1.6–1.9(m, 2H), 0.98(S, 9H), 0.95(S, 9H), [α]$_D^{25}$= +3.9(C=1.0,CHCl$_3$)

Step N—(+)Methyl erythro-(3R,5S)-3,5-di-(tert-butyldiphenylsilyloxy)-6-oxo-hexanoate (a compound D)

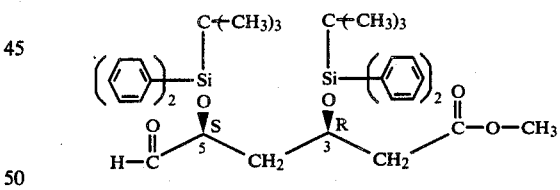

56 mg of the product of Step M above, dissolved in 8.6 ml of ethyl acetate and cooled to −78° C., is treated with a stream of ozone introduced below the surface of the solution, generated externally via a Welsbach Ozonator, for three minutes at which time a blue tint develops in the solution. 45 mg of triphenylphosphine dissolved in one ml ethyl acetate is added and the mixture becomes colorless. After warming to room temperature the solvent is evaporated and the residue purified by a thick layer chromatography on silica gel with 3.1 hexane-diethyl ether to a colorless oil. IR(CHCl$_3$) 1736 (C=O), [α]$_D^{25}$= +2.24(C=1.61,CHCl$_3$), 200 MHz NMR (CDCl$_3$), 9.3(s, 1H), 7.3–7.7(m, 20 H), 4.43[t(J=6 Hz)1H], 4.09[t(J=6 Hz)1H], 3.5(s, 3H), 2.3[d(J=6 Hz)2H], 1.94[t(J=6 Hz)2H], 1.05(s, 9H), 0.96(s, 9H)

Step O, (E)-methyl erythro-(3R,5S)-3.5-di-(diphenyl-5-butyl-siloxy)-7-phenyl-hept-6-enoate (a compound E)

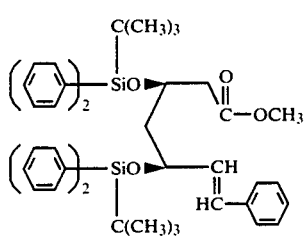

0.28 g (0.72 mmol) of benzyltriphenylphosphonium chloride is suspended in 2 ml of dry tetrahydrofuran (THF) and 0.4 ml of 1.55M solution of n-butyl lithium (in THF) is added at −10°. The mixture is stirred at the reduced temperature for 40 minutes. To the resulting solution, is added 0.47 g (0.72 mmol) of the aldehyde product of Step N, above, 1 in 2 ml of dry THF. The resulting mixture is maintained at 0° for 18 hours, and then diluted with 50 ml methylene chloride, washed with water, the organic phase separated and dried and a residue obtained by evaporation.

The residue is chromatographed on silica using hexane:ethyl acetate (4:1) as eluant system to obtain the olefinic title product of this step.

Step P, (E)-methyl-(3R,5S)-erythro-3,5-dihydroxy-7-phenyl-hept-6-enoate.

A solution of 455 mg (0.63 mmol) of the diprotected-olefinic product of Step O, above, 0.3 ml (5 mmol) of glacial acetic acid, and 5 ml (5 mmol) of 1M tetrabutylammonium fluoride (TBAF) solution in THF, is stirred at room temperature for 18 hours. The mixture is then diluted with 100 ml of methylene chloride, washed with water, the organic phase separated dried, evaporated and the residue chromatographed on silica gel using ethyl acetate as eluant to obtain refined title product of this example.

EXAMPLE 2
(E)-Trans-6-(2-phenylethenyl)-4-hydroxy-tetrahydropyran-2-one, (a compound I'''; 4R,6S form).

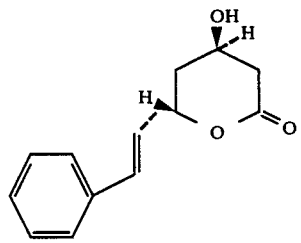

60 m.g. (0.24 mmol) of the dihydroxy ester product of Example 1 is dissolved in 1 ml of dioxane, and the solution cooled in an ice bath. 0.3 ml of 1N sodium hydroxide is then added. After 10 minutes the mixture is acidified (with dilute hydrochloric acid), and then extracted with two 10 ml portions of methylene chloride. The extract is taken to dryness by evaporating, and the resulting residue refluxed in toluene for 5 hours. The mixture is then evaporated. The resulting residue is chromatographed on silica gel, eluting with ethyl acetate and the title product is recovered.

EXAMPLE 3
(E)-Sodium erythro-3,5-dihydroxy-7-(2'-[4"-fluorophenyl]naphth-1'-yl)hept-6-enoate (3R,5S form),

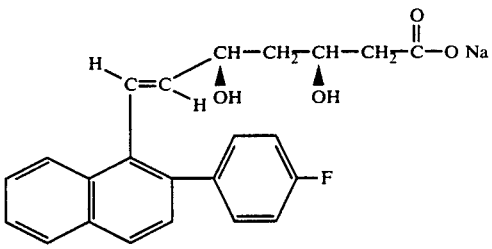

Step A: (E)-Methyl erythro-3,5-di-(diphenyl-t-butylsiloxy)-7-(2'-[4"-fluorophenyl]naphth-1'-yl)hept-6-enoate (3R,5S form)

Repeating the procedure of Step O of Example 1, but employing 555 mg (0.85 mmol) of the title aldehyde product of step N and 450 mg (0.85 mmol) of 1-[2'-(4"-fluorophenyl)-naphth-1-yl]methyl triphenyl phosphonium chloride, and 0.55 ml of 1.55M butyllithium solution, there is obtained the title olefinic product of this step which is recovered by chromatography.

Step B: Sodium trans-3,5-dihydroxy-7-(2'-[4"-fluorophenyl]-naphth-1'-yl)hept-6-enoate(3R,5S form).

400 mg (0.47 mmol) of the di-protected olefinic product of Step A of this example is deprotected using tetrabutylammonium fluoride according to the procedure of Step B of Example 2, to obtain the corresponding Compound I' which is treated with 1 equivalent of 1N sodium hydroxide solution in dioxane, the mixture washed with ether, and the aqueous phase is retained and on lyophilisation yields the product of this Example.

EXAMPLE 4
(E)-Sodium erythro-7-[1'-methyl-3'-(4"-fluorophenyl)indol-2'-yl]-3,5-dihydroxyhept-6-enoate (3R,5S form).

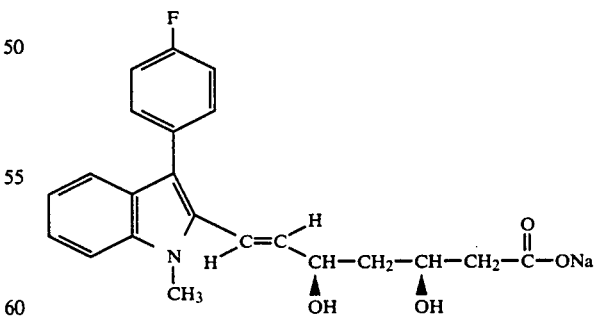

Step A, (E)-Methyl-erythro-7-[1'-methyl-3'-(4"-fluorophenyl)indol-2'-yl]-3,5 di-(diphenyl-t-butylsiloxy)hept-6-enoate (3R,5S form).

Following the procedure of Step O of Example 1, but using 0.59 g (0.90 mmol) of the title aldehyde product of step N thereof, and 482 mg (0.90 mmol) of [1'-methyl-3'-(4"-fluorophenyl)indol-2'-yl]methyl-triphenyl phosphonium chloride, and treatment with a solution of butyl lithium the title di-protected olefinic ester of this step is obtained.

Step B, (E)-sodium erythro-7-[1'-methyl-3-(4"-fluorophenyl)indol-2'-yl]3,5-dihydroxyhept-6-enoate (3R,5S).

400 mg (0.49 mmol) of the di-protected ester obtained in Step A of this example is treated with TBAF as described in Step P of Example 1, above, to obtain the corresponding diol-ester (a compound I') which upon treatment with an equivalent of 1N sodium hydroxide followed by lypholization, yields the title sodium salt product of this example.

EXAMPLE 5

Repeating the procedure of Example 1, but in Step M employing in place of the methyl ester used therein, an approximately equivalent amount of
(a) ethyl;
(b) isopropyl ester; or
(c) t-butyl ester (as a compound A);
there is accordingly obtained the analogous:
(a) ethyl;
(b) isopropyl; and
(c) t-butyl esters of the products.

EXAMPLE 6

(E)-Trans-6-(2-phenylethenyl)-4-hydroxy-tetrahydropyran-2-one (4R,6 S form).

A solution of 91 mg (0.13 mmol) of the product of step O of Example 1, 0.06 ml (1 mmol) of glacial acetic acid and 1 ml (1 mmol) of 1M TBAF solution in THF, is stirred at room temperature for 18 hours, followed by heating the mixture for 2 hrs. at 80° C. The mixture is diluted with 20 ml of $CH_2Cl_2$, washed with water, the organic phase separated, dried, evaporated, and the residue chromatographed on silica gel using ethyl acetate as eluant. The title product of this example (14 mg) is isolated.

What is claimed is:

1. A method of preparing a compound of formula D:

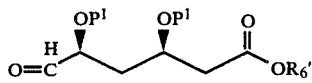

in single enantiomeric form in which $P^1$ is a trisubstituted silyl radical having at least 2 bulky radicals selected from the group consisting of (a) tertiary alkyl ($C_4$ to $C_8$) groups, and (b) phenyl which may be unsubstituted or substituted by up to 2 of any of lower alkyl ($C_1$–$C_4$), chloro, nitro, trifluoromethyl, or mono-substituted in the para-position by phenyl or benzyl which may be unsubstituted, or in turn substituted by one or two of such substituted groups as defined, and any non-bulky radical is unbranched alkyl having from 1 to 4 carbon atoms; and
$R_6$, is alkyl having from 1 to 3 carbon atoms, n-butyl, i-butyl, t-butyl or benzyl; comprising
(a) reacting a compound of formula V:

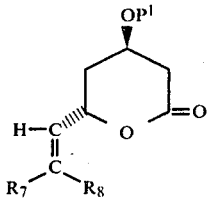

wherein each of $R_7$ and $R_8$ is, independently, a hydrogen atom or alkyl having from 1 to 6 carbon atoms; and $P^1$ is as defined; under essentially anhydrous conditions, at about −10° to +10° C., with a compound of the formula $$M-OR_6'$$

in which $R_6'$ is as defined and M is an alkali metal, in an alcohol of the formula $$R_6'-OH$$

in which $R_6'$ is as defined to form a reaction product;
(b) quenching said reaction product with an aqueous solution, to form the corresponding compound of formula A:

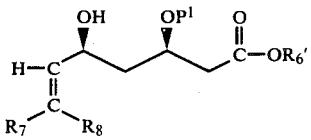

in which $P^1$, $R_6'$, $R_7$ and $R_8$ are as defined;
(c) reacting said compound A with a compound of the formula B:

$$P^1-L \qquad\qquad B$$

in which $P^1$ is as defined and L is a leaving group, in the presence of an acid acceptor, in an inert medium, at a temperature of from about +5° to +40°, under essentially anhydrous conditions; said leaving group being chloro, bromo, or iodo, or an alkyl and aryl sulfonyl radical, in which alkyl is $C_1$–$C_6$ alkyl and aryl is phenyl which may be unsubstituted or mono-substituted by a $C_1$–$C_4$ alkyl, to form the corresponding compound of formula C:

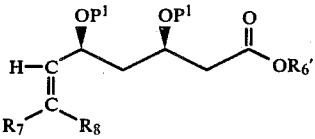

in which $P^1$, $R_6'$, $R_7$ and $R_8$ are as defined; and (d) oxidizing said compound C by reacting which ozone at a temperature of from about −50° to +80° C., in an inert medium to form the corresponding ozonide; and (e) reacting said ozonide with a mild reducing agent to form the corresponding compound D;
with the proviso that compound V has the 4R,6S form and each of compounds A, C, and D have the 3R,5S form.

2. A method of claim 1 wherein $P^1$ is tertiary-butyldiphenylsilyl.

3. A method of claim 1 wherein $R_6'$ is methyl.

4. A method of claim 2 wherein each of $R^7$ and $R^8$ is a hydrogen atom.

5. A method of claim 1 in which L is chloro.

6. A method of claim 1 in which D is methyl (3,R,5S)-3,5-di-(tert.-butyldiphenylsiloxy)-6-oxohexanoate.

7. The method of claim 1 in which $P^1$ has 3 bulky radicals.

8. A method of claim 1 in which any bulky radical of $P^1$ which is aryl is phenyl which may bear 0 or 1 substituent.

9. A method of claim 1 in which $P^1$ is tertiary butyldiphenyl, L is chloro, $R_{6'}$ is methyl and $R_7$ and $R_8$ are each hydrogen.

10. A method of claim 1 in which $R_6'$ is ethyl, each of $R_7$ and $R_8$ is hydrogen, $P^1$ is tertiary-butyldiphenyl, and L is chloro.

11. A method of claim 1 which comprises (f) reacting a compound of formula D with Wittig reagent of formula $X^o$:

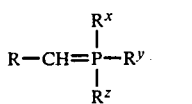

wherein R is a phenyl structure of formula A:

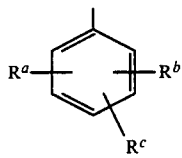

in which each of the $R^a$, $R^b$ and $R^c$ is independently hydrogen; halogen; $C_{1-4}$ alkyl; $C_{1-4}$ haloalkyl; phenyl; or phenyl substituted by halogen; $C_{1-4}$ alkoxy; $C_{2-8}$ alkanoyloxy; $C_{1-4}$ alkyl or $C_{1-4}$ haloalkyl; or $OR^d$ in which $R^d$ is any of hydrogen, $C_{2-8}$ alkanoyl, benzoyl, phenyl, halophenyl, phenyl $C_{1-3}$ alkyl, $C_{1-9}$ alkyl, cinnamyl, $C_{1-4}$ haloalkyl, allyl, cycloalkyl-$C_{1-3}$-alkyl, adamantyl-$C_{1-3}$-alkyl, or substituted phenyl-$C_{1-3}$-alkyl in each of which the substituents are selected from the group consisting of halogen, $C_{1-4}$ alkoxy, $C_{1-4}$ alkyl, or $C_{1-4}$ haloalkyl; a naphthyl or tetrahydronaphthyl structure of the formula B:

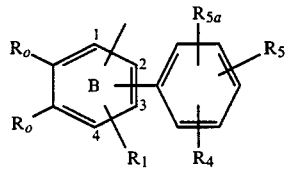

wherein the two $R_o$ groups together form a radical of the formula

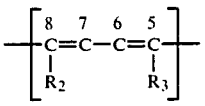

or $-CH_2CH_2CH_2CH_2-$, wherein $R_2$ is hydrogen, $C_{1-3}$alkyl, n-butyl, i-butyl, t-butyl, $C_{1-3}$ alkoxy, n-butoxy, i-butoxy, trifluoromethyl, fluoro, chloro, phenoxy or benzyloxy;

$R_3$ is hydrogen, $C_{1-3}$ alkyl, $C_{1-3}$ alkoxy, trifluoromethyl, fluoro, chloro, phenoxy or benzyloxy;

with the provisos that not more than one of $R_2$ and $R_3$ is trifluoromethyl, not more than one of $R_2$ and $R_3$ is phenoxy, and not more than one of $R_2$ and $R_3$ is benzyloxy;

$R_1$ is hydrogen; $C_{1-6}$ alkyl not containing an asymmetric carbon atom, fluoro, chloro or benzyloxy;

$R_4$ is hydrogen, $C_{1-3}$ alkyl, n-butyl, i-butyl, t-butyl, $C_{1-3}$ alkoxy, n-butyoxy, i-butoxy, trifluoromethyl, fluoro, chloro, phenoxy or benzyloxy;

$R_5$ is hydrogen, $C_{1-3}$ alkyl, $C_{1-3}$ alkoxy, trifluoromethyl, fluoro, chloro, phenoxy or benzyloxy;

$R_{5a}$ is hydrogen, $C_{1-2}$ alkyl, $C_{1-2}$ alkoxy, fluoro or chloro;

with the provisos that not more than one of $R_4$ and $R_5$ is trifluoromethyl, not more than one of $R_4$ and $R_5$ is phenoxy, and not more than one of $R_4$ and $R_5$ is benzyloxy;

with the proviso that on ring B the free valence and ring A are ortho- to each other; or an indol-type radical of the formula C:

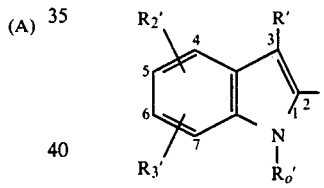

wherein one of R' and $R_o'$ is

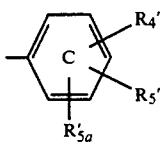

and the other is primary or secondary $C_{1-6}$ alkyl not containing an asymmetric carbon atom, $C_{3-6}$ cycloalkyl or phenyl$(CH_2)_m-$, wherein $R_4'$ is hydrogen, $C_{1-3}$ alkyl, n-butyl, i-butyl, t-butyl, $C_{1-3}$ alkoxy, n-butoxy, i-butoxy, trifluoromethyl, fluoro, chloro, phenoxy or benzyloxy;

$R_5'$ is hydrogen, $C_{1-3}$ alkyl, $C_{1-3}$ alkoxy, trifluoromethyl, fluoro, chloro, phenoxy or benzyloxy;

$R_{5a}'$ is hydrogen, $C_{1-2}$ alkyl, $C_{1-2}$ alkoxy, fluoro or chloro; and m is 1, 2 or 3;

with the provisos that both $R_5'$ and $R_{5a}'$ must be hydrogen when $R_4'$ is hydrogen; $R_{5a}'$ must be hydrogen when $R_5'$ is hydrogen; not more than one of $R_4'$ and $R_5'$ is trifluoromethyl; not more than one of $R_4'$ and $R_5'$ is phenoxy and not more than one of $R_4'$ and $R_5'$ is benzyloxy;

$R_2'$ is hydrogen, $C_{1-3}$ alkyl, n-butyl, i-butyl, t-butyl, $C_{3-6}$ cycloalkyl, $C_{1-3}$ alkoxy, n-butoxy, i-butoxy, trifluoromethyl, fluoro, chloro, phenoxy or benzyloxy;

$R_3'$ is hydrogen, $C_{1-3}$ alkyl, $C_{1-3}$ alkoxy, trifluoromethyl, fluoro, chloro, phenoxy or benzyloxy; with the provisos that $R_3'$ must be hydrogen when $R_2'$ is hydrogen; not more than one of $R_2'$ and $R_3'$ is trifluoromethyl; not more than one of $R_2'$ and $R_3'$ is phenoxy; and not more than one of $R_2'$ and $R_3'$ is benzyloxy; and each of $R^x$, $R^y$ and $R^z$ is phenyl which is unsubstituted or substituted by one or two $C_1$–$C_4$ alkyl or chloro substituents, under essentially anhydrous conditions, in an inert medium, at a temperature of from $-15°$ to $+5°$ C., to obtain the corresponding compound of formula E:

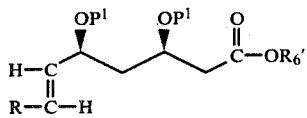

in which $P^1$, $R_6'$ and R are as defined; and (g) reacting said compound E with (1) a mixture of acetic acid and tetrabutylammonium fluoride in tetrahydrofuran, (2) methanolic hydrogen chloride or (3) fluoride anion at a temperature of from about $+20°$ to $+60°$ C. to form the corresponding compound of the formula I':

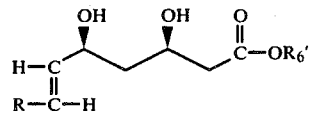

in which R and $R_6'$ are as defined; with the proviso that compound V has the 4R,6S form and compounds A, C, D, E and I' have the 3R,5S form.

12. A method of claim 11 in which each of $R^x$, $R^y$ and $R^z$ is unsubstituted phenyl.

13. A method of claim 11 in which R is 1-methyl-3-(4'-fluorophenyl)indol-2-yl.

14. A method of claim 11 in which R is of type A.

15. A method of claim 11 in which R is of type B.

16. A method of claim 11 in which R is of type C.

* * * * *